(12) United States Patent
Hughes et al.

(10) Patent No.: US 6,335,316 B1
(45) Date of Patent: Jan. 1, 2002

(54) METHOD FOR ADMINISTERING ACYLATED INSULIN

(75) Inventors: Benjamin Lee Hughes, Indianapolis; Ronald Keith Wolff, Carmel, both of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/523,090

(22) Filed: Mar. 10, 2000

Related U.S. Application Data

(62) Division of application No. 09/182,850, filed on Oct. 29, 1998, now Pat. No. 6,051,551.
(60) Provisional application No. 60/064,439, filed on Oct. 31, 1997, now abandoned.

(51) Int. Cl.[7] .................. A61K 38/28; A61K 38/00; C07K 5/00; C07K 7/00
(52) U.S. Cl. .................. 514/3; 514/12; 530/300; 530/324
(58) Field of Search .................. 514/3, 12; 530/324, 530/300

(56) References Cited

U.S. PATENT DOCUMENTS 6,051,551 A * 4/2000 Hughes et al. .................. 514/3

* cited by examiner

*Primary Examiner*—Avis M. Davenport
(74) *Attorney, Agent, or Firm*—Lynn D. Apelgren; James J. Kelley

(57) ABSTRACT

The invention relates to a method of administering a fatty acid-acylated insulin or insulin analog by inhalation, a method for treating diabetes by administering a fatty acid-acylated insulin or insulin analog by inhalation, and a method for treating hyperglycemia by administering a fatty acid-acylated insulin or insulin analog by inhalation.

47 Claims, No Drawings

METHOD FOR ADMINISTERING ACYLATED INSULIN

CROSS-REFERENCE

This application is a divisional of Ser. No. 09/182,850 now U.S. Pat. No. 6,051,551 filed Oct. 29, 1998, which claims the benefit of U.S. Provisional Application No. 60/064,439, filed Oct. 31, 1997, abandoned.

BACKGROUND OF THE INVENTION

1. Field of the Invention

The invention is in the field of human medicine. More particularly, the invention is in the field of the treatment of diabetes and hyperglycemia.

2. Description of Related Art

Diabetes mellitus is a serious and chronic disorder that affects 6% of the world's population and all ethnic groups. In the United States, approximately 5% of the population has diabetes. Symptoms of diabetes include hyperglycemia and reduced production or release of insulin. Diabetes mellitus is classified into two types, type I diabetes or insulin-dependent diabetes mellitus (IDDM) and type II diabetes or non-insulin-dependent diabetes mellitus (NIDDM). Type I diabetes, in which the pancreas has stopped producing insulin, affects 10% of all diabetics, often begins in childhood and is known as juvenile onset diabetes. In the more prevalent type II diabetes, affecting 90% of all diabetics, the pancreas can produce insulin, but insulin secretion in response to meals is diminished, and the diabetic's tissues, are not as responsive to insulin as tissues from a non-diabetic. Type II diabetes is also known as adult onset diabetes.

Diminished response to or low levels of insulin result in chronic high levels of blood glucose, which gradually alters normal body chemistry and leads to failure of the microvascular system in many organs. This leads to dire consequences. For example, in the United States, diabetes is the largest cause of blindness, is involved in about 70%. of amputations, and is the cause of kidney failure in 33% of patients requiring dialysis. Medical treatment of side effects of diabetes and lost productivity due to inadequate treatment of diabetes are estimated to have an annual cost of about $40 billion in the United States alone.

It has long been a goal of insulin therapy to mimic the pattern of endogenous insulin secretion in normal individuals. The daily physiological demand for insulin fluctuates and can be separated into two phases: (a) the absorptive phase requiring a pulse of insulin to dispose of the meal-related blood glucose surge, and (b) the post-absorptive phase requiring a sustained delivery of insulin to regulate hepatic glucose output for maintaining optimal fasting blood glucose. Accordingly, effective therapy for people with diabetes generally involves the combined use of two types of exogenous insulin formulations: a fast-acting meal time insulin provided by bolus injections and a long-acting, so-called, basal insulin, administered by injection once or twice daily to control blood glucose levels between meals.

The 9-year Diabetes Control and Complications Trial (DCCT), which involved 1441 type I diabetic patients, demonstrated that maintaining blood glucose levels within close tolerances reduces the frequency and severity of diabetes complications. Conventional insulin therapy involves only two injections per day. ThLe intensive insulin therapy in the DCCT study involved three or more injections of insulin each day. In this study the incidence of diabetes-side effects was dramatically reduced. For example, retinopathy was reduced by 50–76%, nephropathy by 35–56%, and neuropathy by 60% in patients employing intensive therapy.

Unfortunately, many diabetics are unwilling to undertake intensive therapy due to the discomfort associated with the many injections required to maintain close control of glucose levels. A non-injectable form of insulin is desirable for increasing patient compliance with intensive insulin therapy and lowering their risk of complications. Many investigators have studied alternate routes for administering insulin, such as oral, rectal, transdermal, and nasal routes. So far, these types of administration have not been effective due to poor insulin absorption, low serum insulin concentration, irritation at the site of delivery, or lack of significant decrease in serum glucose levels.

Due to its small relatively small molecular weight (5,800 daltons) insulin seems to be an ideal candidate for administration through inhalation into the lungs. In fact, administration of insulin as an inhalation aerosol to the lung was first reported in 1925. In the past 70 years, numerous human and animal studies have shown that some insulin formulations are well absorbed by the lungs. After administration by inhalation, small-sized proteins are absorbed and reach maximum plasma concentrations more quickly than larger proteins. As expected for a small protein, the previously-studied insulin formulations typically exhibit a rapid rise followed by a rapid fall in plasma insulin levels.

The intense effort devoted to developing an inhaled insulin formulation has failed to achieve a system for slower uptake and longer duration of action of insulin is needed to control blood glucose between meals, and overnight. Therefore, there remains a need for an effective system for administration of a long-acting insulin by inhalation.

SUMMARY OF THE INVENTION

The present invention is a method for administering long-acting, soluble insulin by inhalation. The invention also encompasses the use of a fatty acid-acylated human insulin or a fatty acid-acylated insulin analog in the manufacture of a medicament for the treatment of diabetes or hyperglycemia by inhalation, which treatment comprises administering to a patient in need thereof an effective amount of the medicament using an inhalation device, such that the medicament is deposited in the lungs of the patient. The present invention solves two problems currently not addressed by the art. First, previous pulmonary methods for delivering insulin do not provide adequate time action to control blood glucose between meals and overnight. Second, presently known soluble, long-acting insulins and insulin derivatives are delivered by subcutaneous injection, which involves the inconvenience of preparing a sample for injection, and the pain of a needle-stick. According to the present invention, a patient in need of insulin to control blood glucose levels will achieve advantageous slow uptake and prolonged persistence in the blood of-acylated insulin compared to inhalation of non-acylated insulin, and reduced inconvenience and pain compared with subcutaneous delivery. Preferably, the acylated insulin is delivered to the lower airway of the patient. The acylated insulin can be delivered in a carrier, as a solution or suspension, or as a dry powder, using any of a variety of devices suitable for administration by inhalation. The acylated insulin can be administered using an inhalation device such as a nebulizer, a metered-dose inhaler, a dry powder inhaler, a sprayer, and the like. Preferably, the acylated insulin is delivered-in a particle size effective for reaching the lower airways of the lung, preferably less than about 10 microns mass median aerodynamic diameter (MMAD), preferably about 1 to about 5 microns MMAD, and more preferably about 1 to about 3 microns MMAD or from about 1 to about 2 microns MMAD, and most preferably from about 2 to about 3 microns MMAD. Preferred acylated insulins include a fatty acid-acylated insulin and a fatty acid-acylated insulin analog. The invention also provides a method for administering acylated insulin or acylated insulin analog together with insulin or insulin analog to a patient in need thereof by inhalation. Administering such combinations of acylated and un-acylated insulins provides both post-prandial and basal control of blood glucose levels. Because the method avoids injections, patient comfort is improved, and patient compliance increased compared with conventional insulin delivery methods.

DETAILED DESCRIPTION OF THE INVENTION

The term "fatty acid-acylated insulin protein" refers to a protein, selected from the group consisting of mammalian insulin and mammalian insulin analogs, that is acylated with a fatty acid that is bonded through an amide bond formed between the acid group of the fatty acid and an amino group of the protein, and pharmaceutically acceptable salts and complexes thereof. The amino group may be the α-amino group of an N-terminal amino acid of the protein, or may be the ε-amino group of a Lys residue of the protein. The acylation of insulin with a fatty acid is disclosed in Japanese patent application 1-254,699. See also, Hashimoto, et al., *Pharmaceutical Research*, 6:171–176 (1989), and Lindsey, et al., *Biochemistry* 121:737–745 (1971). Further disclosure of fatty acid-acylated insulins and fatty acid-acylated insulin analogs, and of methods for their synthesis, is found in Baker, et al., U.S. Pat. No. 5,693,609, issued Dec. 2, 1997; Havelund, et al., WO95/07931, published Mar. 23, 1995; and Jonassen, et al., WO96/29342, published Sep. 26, 1996. These disclosures are expressly incorporated herein by reference for describing acylated insulins and acylated insulin analogs, and for enabling preparation of the same.

A fatty acid-acylated insulin or insulin analog may be acylated at one or more of the three amino groups that are present in mammalian insulin and in most insulin analogs. Mono-acylated insulins are acylated at a single amino group. Di-acylated insulins are acylated at two amino groups. Tri-acylated insulins are acylated at three amino groups. The terms "fatty acid-acylated insulin" and "fatty acid-acylated insulin analog" refer to preparations of fatty acid-acylated insulin and fatty acid-acylated insulin analogs, respectively, which are herein referred to collectively as fatty acid-acylated insulin protein. Typically, the population of acylated molecules is relatively homogeneous with respect to the site or sites of acyation, such as: Nε-mono-acylated insulin protein, B1-Nε-mono-acylated insulin or insulin analog; A1-Nα-mono-acylated insulin or insulin analog; A1-Nα, B1-Nα-di-acylated insulin or insulin analog; Nε, A1-Nα-di-acylated insulin or insulin analog; Nε, B1-Nα-di-acylated insulin or insulin analog, and Nε, A1-Nα, B1-Nα-tri-acylated insulin or insulin analog. The terms fatty acid-acylated insulin and fatty acid-acylated insulin analog also refer to preparations wherein the population of acylated molecules has heterogeneous acylation. In the latter case, these terms include mixtures of mono-acylated and di-acylated proteins, mixtures of mono-acylated and tri-acylated proteins, mixtures of di-acylated and tri-acylated proteins, and mixtures of mono-acylated, di-acylated, and tri-acylated proteins. Preferred acylated insulins include mono-acylated insulin, particularly mono-acylated insulin acylated at positions B1 or B29, preferably B29. Preferred acylated insulin analogs are mono-acylated at B1, or at the Nε-amino group of lysine. Examples of preferred fatty acid-acylated insulin proteins are B29-Nε-palmitoyl-human insulin, B29-Nε-myristoyl-desB30-human insulin, B29-Nε-myristoyl-human insulin, B28-Nε-palmitoyl-LysB28, ProB29-human insulin analog, and B28-Nε-myristoyl-LysB28, ProB29-human insulin analog.

The verb "acylate" means to form an amide bond between an organic acid and an amino group of a protein. An insulin is "acylated" when one or more of its amino groups is combined in an amide bond with the acid group of an organic acid. Generally, insulin or insulin analogs are acylated by reacting them with an activated acid compound. Activated acids are acyl compounds having carboxylic acid activating groups, such as, activated ester, acid halide, acid azolide, or acid anhydride, and in particular, hydroxybenzotriazide (HOBT), N-hydroxysuccinimide, and derivatives thereof.

The use of activated fatty acid esters, especially N-hydroxysuccinimide esters of fatty acids, is a particularly advantageous means of acylating a free amino acid with a fatty acid. The term "activated fatty acid ester" means a fatty acid which has been activated using general techniques known in the art [*Methods of Enzymology*, 25:494–499 (1972) and Lapidot, et al. *J. of Lipid Res*. 8:142–145 (1967)]. Lapidot, et al. describe the preparation of N-hydroxysuccinimide esters and their use in the preparation of N-lauroyl-glycine, N-lauroyl-L-serine, and N-lauroyl-L-glutamic acid.

The acylation of normal insulin with a fatty acid is disclosed in a Japanese patent application 1-254,699. See also, Hashimoto, et al., *Pharmaceutical Research*, 6:171–176 (1989), and Lindsey, et al., *Biochemistry* 121:737–745 (1971). Further disclosure of acylated insulins and acylated insulin analogs, and of methods for their synthesis, is found in Baker, et al, U.S. Ser. No. 08/342,931, filed Nov. 17, 1994; Havelund, et al., WO95/07931, published Mar. 23, 1995; Jonassen, et al., WO96/29342, published Sep. 26, 1996; and Hansen, L., WO98/02460, published Jan. 22, 1998. The entirety of each these publications is expressly incorporated herein by reference.

To selectively acylate the ε-amino group, various protecting groups may be used to block the α-amino group during the coupling. The selection of a suitable protecting group is known to one skilled in the art and includes, for example, p-methoxybenzoxycarbonyl (pmZ). Preferably, the ε-amino group is acylated in a one-step synthesis without the use of amino-protecting groups. A process for selective acylation at the Nε-amino group of Lys in insulin is disclosed and claimed in U.S. Pat. No. 5,646,242, issued Jul. 8, 1997, the entire disclosure of which is incorporated expressly by reference. A process for preparing a dry powder of an acylated protein is disclosed in U.S. Pat. No. 5,700,904, issued Dec. 23, 1997, the entire disclosure of which is incorporated expressly herein by reference.

The term "fatty acid" means a saturated or unsaturated fatty acid having from 6 to 18 carbon atoms. Preferred fatty acids have from 10 to 16 carbon atoms. Yet a more preferred group of fatty acids have from 13 to 17 carbon atoms. A highly preferred group of fatty acids have 14 or 16 carbon atoms, and more preferably 14 carbon atoms.

The term "insulin" as used herein refers to mammalian insulin, such as bovine, porcine or human insulin, whose sequences and structures are known in the art. Bovine, porcine, and human insulin are preferred mammalian insulins; human insulin is more preferred. The amino acid sequence and spatial structure of human insulin are well-known. Human insulin is comprised of a twenty-one amino acid A-chain and a thirty amino acid B-chain which are cross-linked by disulfide bonds. A properly cross-linked human insulin contains three disulfide bridges: one between position 7 of the A-chain and position 7 of the B-chain, a second between position 20 of the A-chain and position 19 of the B-chain, and a third between positions 6 and 11 of the A-chain.

The term "insulin analog" means proteins that have an A-chain and a B-chain that have substantially the same amino acid sequences as the A-chain and B-chain of human insulin, respectively, but differ from the A-chain and B-chain of human insulin by having one or more amino acid deletions, one or more amino acid replacements, and/or one or more amino acid additions that do not destroy the insulin activity of the insulin analog. Preferred insulin analogs include the monomeric insulin analogs, and desB30 human insulin analog.

One type of insulin analog, "monomeric insulin analog," is well-known in the art. These are fast-acting analogs of human insulin, including, for example, human insulin wherein Pro at position B28 is substituted with Asp, Lys, Leu, Val, or Ala, and wherein Lys at position B29 is Lys or is substituted with Pro, and also, AlaB26-human insulin, des(B28–B30) human insulin, and des(B27) human insulin. These, and other monomeric insulin analogs are disclosed in Chance, et al., U.S. Pat. No. 5,514,646, issued May 7, 1996; Chance, et al., U.S. patent application Ser. No. 08/255,297; Brems, et al., *Protein Engineering*, 6:527–533 (1992); Brange, et al., EPO Publication No. 214,826 (published Mar. 18, 1987); Brange, et al., *Current Opinion in Structural Biology*, 1:934–940 (1991); Balschmidt, P., et al., EPO Publication No. 837,072 (published Apr. 22, 1998). These disclosures are expressly incorporated herein by reference for describing monomeric insulin analogs. The monomeric insulin analogs employed in the present formulations are properly cross-linked at the same positions as is human insulin.

Insulin analogs may also have replacements of the amidated amino acids with acidic forms. For example, Asn may be replaced with Asp or Glu. Likewise, Gln may be replaced with Asp or Glu. In particular, AsnA18, AsnA21, or AsnB3, or any combination of those residues, may be replaced by Asp or Glu. Also, GlnA15 or GlnB4, or both, may be replaced by either Asp or Glu. Particularly preferred insulin analogs are those having, optionally, among other replacements or deletions, Asp at B21, or Asp at B3, or both replacements.

Insulin and insulin analogs used to prepare the fatty acid-acylated insulins that are administered in the present invention can be prepared by any of a variety of recognized peptide synthesis techniques including classical (solution) methods, solid phase methods, semi-synthetic methods, and more recent recombinant DNA methods. For example Chance, et al., U.S. Pat. No. 5,514,646, EPO publication number 383,472, Brange, et al. EPO 214,826, and Belagaje, et al., U.S. Pat. No. 5,304,473, disclose the preparation methods for insulin and insulin analogs. The entirety of each these publications is expressly incorporated herein by reference.

The term "complex" means a compound in which a transition metal is coordinated to at least one ligand. Ligands include nitrogen-containing molecules, such as insulins, peptides, amino acids, and TRIS, among many other compounds. The fatty acid-acylated insulin or fatty acid-acylated insulin analog used in the present invention are preferably in a complex with one or more divalent zinc ions, wherein the protein molecule acts a ligand of the zinc ions.

The term "preservative" refers to a compound added to a pharmaceutical formulation to act as an anti-microbial agent. A parenteral formulation must meet guidelines for preservative effectiveness to be a commercially viable multi-use product. Among preservatives known in the art as being effective and acceptable in parenteral formulations are benzalkonium chloride, benzethonium, chlorohexidine, phenol, m-cresol, benzyl alcohol, methylparaben, chlorobutanol, o-cresol, p-cresol, chlorocresol, phenylmercuric nitrate, thimerosal, benzoic acid, and various mixtures thereof. See, e.g., Wallhauser, K., *Develop. Biol. Standard*, 24: 9–28 (Basel, S. Krager, 1974). Certain phenolic preservatives, such as phenol and m-cresol, are known to bind to insulin-like molecules and thereby to induce conformational changes that increase either physical or chemical stability, or both [Birnbaum, et al., *Pharmac. Res.* 14: 25 (1997); Rahuel-Clermont, et al., *Biochemistry* 36: 5837–5845 (1997)]. M-cresol and phenol are preferred preservatives in formulations of the fatty acid-acylated insulin proteins used in the present invention.

The term "buffer" or "pharmaceutically acceptable buffer" refers to a compound that is known to be safe for use in insulin formulations and that has the effect of controlling the pH of the formulation at the pH desired for the formulation. Pharmaceutically acceptable buffers for controlling pH at a moderately acid pH to a moderately basic pH include such compounds as phosphate, acetate, citrate, TRIS, arginine, or histidine.

The term "isotonicity agent" refers to a compound that is tolerated physiologically and imparts a suitable tonicity to a formulation to prevent the net flow of water across the cell membrane. Compounds, such as glycerin, are commonly used for such purposes at known concentrations. Other acceptable isotonicity agents include salts, e.g., NaCl, dextrose, mannitol, and lactose. Glycerol at a concentration of 12 to 25 mg/mL is preferred as an isotonicity agent.

The abbreviations "MMAD" and "MMEAD" are well-known in the art, and stand for "mass median aerodynamic diameter" and "mass median equivalent aerodynamic diameter," respectively. The terms are substantially equivalent. The "aerodynamic equivalent" size of a particle is the diameter of a unit density sphere which exhibits the same aerodynamic behavior as the particle, regardless of actual density or shape. MMAD is determined using a cascade impactor, which measures-the particle size as a function of the aerodynamic behavior of the particle in a high velocity airstream. The median (50%) particle size is obtained from a linear regression analysis of the cumulative distribution data.

One vehicle for a fatty acid-acylated insulin protein is Humulin® R Diluent. A formulation with this vehicle includes a fatty acid-acylated insulin protein at the desired concentration, m-cresol at about 2.5 mg/ml, glycerol at about 16 mg/mL, and zinc at about 0.016 mg/mL, the formulation being at pH about 7.4. An alternative vehicle is Humulin® L Diluent which includes a fatty acid-acylated insulin protein at the desired concentration; zinc oxide at about 0.12 mg/mL to about 0.3 mg/mL, preferably about 0.17 mg/mL; sodium acetate at about 6.5 mg/mL to about 7.5 mg/mL, preferably about 7.0 mg/mL; and methylparaben at about 0.8 mg/mL to about 1.2 mg/mL, preferably about 1.0 mg/mL. Certain formulations of insulin protein with zinc are known as Lente® insulins. Additional suitable formulations of insulin protein with zinc and of Lente® insulins are known to those of skill in the art.

Fatty acid-acylated insulin activity is administered by inhalation in a dose effective to increase circulating insulin protein levels and/or to lower circulating glucose levels. Such administration can be effective for treating disorders such as diabetes or hyperglycemia. Achieving effective doses of fatty acid-acylated insulin protein requires administration of an inhaled dose of more than about 0.5 µg/kg to about 200 µg/kg fatty acid-acylated insulin protein. Preferably the dose is about 5 µg/kg to about 100 µg/kg, about 10 µg/kg to about 100 µg/kg, about 20 µg/kg to about 100 µg/kg, or about 30 µg/kg to about 100 µg/kg. More preferably, the dose is from about 10 µg/kg to about 60 µg/kg, 20 µg/kg to about 60 µg/kg, or 30 µg/kg to about 60 µg/kg. A therapeutically effective amount can be determined by a knowledgeable practitioner, who will take into account factors including insulin protein level, the physical condition of the patient, the patient's pulmonary status, the potency and bioavailability of the fatty acid-acylated insulin protein, whether the fatty acid-acylated protein is administered together with another insulin, such as a fast-acting, or meal-time insulin, cr with other therapeutic agents, or other factors known to the medical practitioner. Effective therapy can include starting at a low dose of fatty acid-acylated insulin protein, monitoring blood glucose levels, and increasing the dose of fatty acid-acylated insulin protein as required to achieve desired blood glucose levels.

According to the invention, fatty acid-acylated insulin protein is delivered by inhalation to achieve advantageous slow uptake of fatty acid-acylated insulin protein compared to inhalation of non-acylated insulin protein. Administration by inhalation results in pharmacokinetics comparable to subcutaneous administration of insulins. Subcutaneous injection of insulins, such as fatty acid-acylated insulin protein, typically results in a slow rise in the level of insulin until blood levels reach a maximum several hours, typically about 3 hours, after injection. Levels of insulins, such as fatty acid-acylated insulin proteins, then, typically, drop to basal levels with a half-life of about 5 to about 8 hours. Inhalation of native or other non-acylated forms of insulin leads to a rapid rise in the level of circulating insulin followed by a rapid fall in insulin level. For example, after inhalation, levels of non-acylated insulin rise to a maximum in only about 20 to about 30 min and return to basal levels with a half-life of about one hour. Advantageously, inhalation of fatty acid-acylated insulin protein results in slow uptake of the fatty acid-acylated insulin protein into the blood followed by a slow fall in the blood level. Preferably, inhaled fatty acid-acylated insulin protein reaches peak levels in the blood about 3 to about 5 hours after inhalation, followed by a return to basal levels with a half-life of about 5 to about 8 hours, preferably about 5 hours. Different inhalation devices typically provide similar pharmacokinetics when similar particle sizes and similar levels of lung deposition are compared.

According to the present invention, a fatty acid-acylated insulin protein can be delivered by any of a variety of inhalation devices and methods known in the art for administration of insulin, or other proteins, by inhalation [Rubsamen, U.S. Pat. No. 5,364,838, issued Nov. 15, 1994; Rubsamen, U.S. Pat. No. 5,672,581, issued Sep. 30, 1997; Platz, et al., WIPO publication No. WO96/32149, published Oct. 17, 1996; Patton, et al., WIPO publication No. WO95/24183, published Sep. 14, 1995; Johnson, et al., U.S. Pat. No. 5,654,007, issued Aug. 5, 1997; Goodman, et al., U.S. Pat. No. 5,404,871, issued Apr. 11, 1995; Rubsamen, et al., U.S. Pat. No. 5,672,581, issued Sep. 30, 1997; Gonda, et al., U.S. Pat. No. 5,743,250, issued Apr. 28, 1998; Rubsamen, U.S. Pat. No. 5,419,315, issued May 30, 199; Rubsamen, et al., U.S. Pat. No. 5,558,085, issued Sep. 24, 1996; Gonda, et al., WIPO publication No. WO98/33480, published Aug. 6, 1998; Rubsamen, U.S. Pat. No. 5,364,833, issued Nov. 15, 1994; Laube, et al., U.S. Pat. No. 5,320,094, issued Jun. 14, 1994; Eljamal, et al. U.S. Pat. No. 5,780,014, issued Jul. 14, 1998; Backstrom, et al., U.S. Pat. No. 5,658,878, issued Aug. 19, 1997; Backstrom, et al., 5,518,998, issued May 21, 1996; Backstrom, et al., 5,506,203, issued Apr. 9, 1996; Meezan, et al., U.S. Pat. No. 5,661,130, issued Aug. 26, 1997; Hodson, et al., U.S. Pat. No. 5,655,523, issued Aug. 12, 1997; Schultz, et al., U.S. Pat. No. 5,645,051, issued Jul. 8, 1997; Eisele, et al., U.S. Pat. No. 5,622,166, issued Apr. 22, 1997; Mecikalski, et al., U.S. Pat. No. 5,577,497, Nov. 26, 1996; Mecikalski, et al., U.S. Pat. No. 5,492,112, issued Feb. 20, 1996; Williams, et al., U.S. Pat. No. 5,327,883, issued Jul. 12, 1994; Williams, U.S. Pat. No. 5,277,195, issued Jan. 11, 1994]. The entire disclosure of each of the publications listed above is incorporated expressly herein by reference.

Included among the devices used to administer acylated insulins according to the present invention are those well-known in the art, such as, metered dose inhalers, liquid nebulizers, dry powder inhalers, sprayers;, thermal vaporizers, and the like, and those provided by developing technology, including the AERx® pulmonary drug delivery system being developed by Aradigm Corporation, the dry powder formulation and delivery devices being developed by Inhale Therapeutic Systems, Inc., and the Spiros® dry powder inhaler system being developed by Dura Pharmaceuticals, Inc. Other suitable technology includes electrohydrodynamic aerosolizers. The inhalation device should deliver small particles, e.g., less than about 10 µm MMAD, preferably about 1–5 µm MMAD, for good respirability, and more preferably in the range of about 1 to about 3 µm MMAD, or about 1 to about 2 µm MMAD, and most preferably from about 2 to about 3 µm MMAD.

In addition, the inhalation device must be practical, in the sense of being easy to use, small enough to carry conveniently, capable of providing multiple doses, and durable. Some specific examples of commercially available inhalation devices suitable for the practice of this invention are Turbohaler (Astra), Rotahaler (Glaxo), Diskus (Glaxo), the Ultravent nebulizer (Mallinckrodt), the Acorn II nebulizer (Marquest Medical Products) the Ventolin metered dose inhaler (Glaxo), the Spinhaler powder inhaler (Fisons), or the like. Fatty acid-acylated insulin proteins can be advantageously delivered by a dry powder inhaler or a sprayer. There are several desirable features of a dry powder inhalation device for administering fatty acid-acylated insulin protein. For example, delivery by such inhalation devices is advantageously reliable, reproducible, and accurate.

As those skilled in the art will recognize, the formulation of fatty acid-acylated insulin protein, the quantity of the formulation delivered, and the duration of administration of a single dose depend on the type of inhalation device employed. For some aerosol delivery systems, such as nebulizers, the frequency of administration and length of time for which the system is activated will depend mainly on the concentration of fatty acid-acylated insulin protein in the aerosol. For example, shorter periods of administration can be used at higher concentrations of fatty acid-acylated insulin protein in the nebulizer solution. Devices such as metered dose inhalers can produce higher aerosol concentrations, and can be operated for shorter periods to deliver the desired amount of fatty acid-acylated insulin protein. Devices such as dry powder inhalers deliver active agent until a given charge of agent is expelled from the device. In this type of inhaler, the amount of fatty acid-acylated insulin protein in a given quantity of the powder determines the dose delivered in a single administration.

The particle size of the fatty acid-acylated insulin protein formulation delivered by the inhalation device determines the extent to which the particles are conveyed into the lower airways or alveoli, where deposition is most advantageous because of the large surface area. Conversely, the formulation of the fatty acid-acylated insulin protein will affect the particle size. Preferably, the fatty acid-acylated insulin protein is formulated so that at least about 10% of the fatty acid-acylated insulin protein is deposited in the lower lung, preferably about 10% to about 20%, or more. It is known that the maximum efficiency of pulmonary deposition for mouth-breathing humans is obtained at about 2 $\mu$m to about 3 $\mu$m MMAD. Above about 5 $\mu$m MMAD, pulmonary deposition decreases substantially. Below about 1 $\mu$m MMAD pulmonary deposition decreases, and it becomes difficult to deliver particles with sufficient mass to be therapeutically effective. Preferably, particles of fatty acid-acylated insulin delivered by inhalation have a particle size less than about 10 $\mu$m, preferably in the range of about 1 $\mu$m to about 5 $\mu$m MMAD, and more preferably in the range of about 1 to about 3 $\mu$m MMAD or from about 1 to about 2 $\mu$m MMAD, and most preferably from about 2 to about 3 $\mu$m MMAD. The formulation of fatty acid-acylated insulin is selected to yield the desired particle size in the chosen inhalation device.

Dry powder generation typically employs a method such as a scraper blade or an air blast to generate particles from a solid formulation of fatty acid-acylated insulin protein. The particles are generally generated in a container and then transported into the lung of a patient via a carrier air stream. Typically, in current dry powder inhalers, the force for breaking up the solid and air flow is provided solely by the patient's inhalation. One suitable dry powder inhaler is the Turbohaler manufactured by Astra. Administration by dry powder inhaler is a preferred method for fatty acid-acylated insulin protein.

Formulations of fatty acid-acylated insulin protein for administration from a dry powder inhaler typically include a finely divided dry powder containing fatty acid-acylated insulin protein, but the powder can also include a non-acylated insulin or insulin analog to provide relatively rapid onset, and short duration of action, a bulking agent, buffer, carrier, excipient, another additive, or the like. Additives can be included in a dry powder formulation of fatty acid-acylated insulin protein, for example, to dilute the powder as required for delivery from the particular powder inhaler, to facilitate processing of the formulation, to provide advantageous powder properties to the formulation, to facilitate dispersion of the powder from the inhalation device, to stabilize to the formulation (e.g., antioxidants or buffers), to provide taste to the formulation, or the like.

Advantageously, the additive does not adversely affect the patient's airways. The fatty acid-acylated insulin protein can be mixed with an additive at a molecular level or the solid formulation can include particles of the fatty acid-acylated insulin protein mixed with or coated on particles of the additive. Typical additives include mono-, di-, and polysaccharides; sugar alcohols and other polyols, such as, for example, lactose, glucose, raffinose, melezitose, lactitol, maltitol, trehalose, sucrose, mannitol, starch, or combinations thereof; surfactants, such as sorbitols, diphosphatidyl choline, or lecithin; or the like. Typically an additive, such as a bulking agent, is present in an amount effective for a purpose described above, often at about 50% to about 90% by weight of the formulation. Additional agents known in the art for formulation of a protein such as fatty acid-acylated insulin protein can also be included in the formulation. See, for example, Japanese Pat. No. J04041421, published Feb. 12, 1992 (Taisho Pharmaceutical).

Advantageously for administration as a dry powder, fatty acid-acylated insulin protein is prepared in a particulate form with an MMAD of less than about 10 microns, preferably about 1 to about 5 microns, and more preferably in the range of about 1 to about 3 $\mu$m MMAD, or from about 1 to about 2 $\mu$m MMAD, and, most preferably, from about 2 to about 3 $\mu$m MMAD. The preferred particle size is effective for delivery to the alveoli of the patient's lung. Preferably, the dry powder is largely composed of particles produced so that a majority of the particles have a size in the desired range. Advantageously, at least about 50% of the dry powder is made of particles having a diameter less than about 10 $\mu$m MMAD. Such formulations can be achieved by spray drying, milling, or critical point condensation of a solution containing fatty acid-acylated insulin protein and other desired ingredients.

A spray including fatty acid-acylated insulin protein can be produced by forcing a suspension or solution of fatty acid-acylated insulin protein through a nozzle under pressure. The nozzle size and configuration, the applied pressure, and the liquid feed rate can be chosen to achieve the desired output and particle size. An electrospray can be produced by an electric field in connection with a capillary or nozzle feed. Advantageously, particles of fatty acid-acylated insulin protein delivered by a sprayer have a particle size less than about 10 $\mu$m, preferably in the range of about 1 $\mu$m to about 5 $\mu$m MMAD, and more preferably in the range of about 1 to about 3 $\mu$m MMAD, or about 1 to about 2 $\mu$m MMAD, and most preferably from about 2 to about 3 $\mu$m MMAD. Administration as a spray is a preferred method for fatty acid-acylated insulin protein.

Formulations of fatty acid-acylated insulin protein suitable for use with a sprayer typically include fatty acid-acylated insulin protein in an aqueous solution at a concentration of about 1 mg to about 20 mg of fatty acid-acylated insulin protein per mL of solution. The formulation can include agents such as an excipient, a buffer, an isotonicity agent, a preservative, a surfactant, and, preferably, zinc. The formulation can also include an excipient or agent for stabilization of the fatty acid-acylated insulin protein, such as a buffer, a reducing agent, a bulk protein, or a carbohydrate. Bulk proteins useful in formulating fatty acid-acylated insulin proteins include albumin, protamine, or the like. Typical carbohydrates useful in formulating fatty acid-acylated insulin proteins include sucrose, mannitol, lactose, trehalose, glucose, or the like. The fatty acid-acylated insulin protein formulation can also include a surfactant, which can reduce or prevent surface-induced aggregation of the fatty acid-acylated insulin protein caused by atomization of the solution in forming an aerosol. Various conventional surfactants can be employed, such as polyoxyethylene fatty acid esters and alcohols, and polyoxyethylene sorbitol fatty acid esters. Amounts will generally range between 0.001% and 4% by weight of the formulation. Especially preferred surfactants for purposes of this invention are polyoxyethylene sorbitan monooleate, polysorbate 80, polysorbate 20, or the like. Additional agents known in the art for formulation of a protein such as fatty acid-acylated insulin protein can also be included in the formulation.

Fatty acid-acylated insulin protein can be administered by a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of fatty acid-acylated insulin protein through a capillary tube connected to a liquid reservoir. The solution streaming from the capillary tube is sheared into unstable filaments and droplets as it exits the tube, creating an aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically by employing a piezoelectric transducer. This energy is transmitted to the formulation of fatty acid-acylated insulin protein either directly or through a coupling fluid, creating an aerosol including the fatty acid-acylated insulin protein. Advantageously, particles of fatty acid-acylated insulin protein delivered by a nebulizer have a particle size less than about 10 $\mu$m, preferably in the range of about 1 $\mu$m to about 5 $\mu$m MMAD, and more preferably in the range of about 1 to about 3 $\mu$m MMAD, or about 1 to about 2 $\mu$m MMAD, and most preferably from about 2 to about 3 $\mu$m MMAD.

Formulations of fatty acid-acylated insulin protein suitable for use with a nebulizer, either jet or ultrasonic, typically include fatty acid-acylated insulin protein in an aqueous solution at a concentration of about 1 mg to about 20 mg of fatty acid-acylated insulin protein per mL of solution. The formulation can include agents such as an excipient, a buffer, an isotonicity agent, a preservative, a surfactant, and, preferably, zinc. The formulation can also include an excipient or agent for stabilization of the fatty acid-acylated insulin protein, such as a buffer, a reducing agent, a bulk protein, or a carbohydrate. Bulk proteins useful in formulating fatty acid-acylated insulin proteins include albumin, protamine, or the like. Typical carbohydrates useful in formulating fatty acid-acylated insulin proteins include sucrose, mannitol, lactose, trehalose, glucose, or the like. The fatty acid-acylated insulin protein formulation can also include a surfactant, which can reduce or prevent surface-induced aggregation of the fatty acid-acylated insulin protein caused by atomization of the solution in forming an aerosol. Various conventional surfactants can be employed, such as polyoxyethylene fatty acid esters and alcohols, and polyoxyethylene sorbital fatty acid esters. Amounts will generally range between 0.001 and 4% by weight of the formulation. Especially preferred surfactants for purposes of this invention are polyoxyethylene sorbitan monooleate, polysorbate 80, polysorbate 20, or the like. Additional agents known in the art for formulation of a protein such as fatty acid-acylated insulin protein can also be included in the formulation.

In a metered dose inhaler (MDI), a propellant, fatty acid-acylated insulin protein, and any excipients or other additives are contained in a canister as a mixture including a liquefied compressed gas. Actuation of the metering valve releases the mixture as an aerosol, preferably with a MMAD in the range of less than about 10 $\mu$m, preferably about 1 $\mu$m to about 5 $\mu$m, and more preferably in the range of about 1 to about 3 $\mu$m MMAD, or about 1 to about 2 $\mu$m MMAD, and, most preferably from about 2 to about 3 $\mu$m MMAD. The desired aerosol particle size can be obtained by employing a formulation of fatty acid-acylated insulin protein produced by various methods known to those of skill in the art, including jet-milling, spray drying, critical point condensation, or the like. Preferred metered dose inhalers include those manufactured by 3M or Glaxo and employing a hydrofluorocarbon propellant.

Formulations of fatty acid-acylated insulin protein for use with a metered-dose inhaler device will generally include a finely divided powder containing fatty acid-acylated insulin protein as a suspension in a non-aqueous medium, for example, suspended in a propellant with the aid of a surfactant. The propellant may be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluroalkane-134a), HFA-227 (hydrofluroalkane-227), or the like. Preferably the propellant is a hydrofluorocarbon. The surfactant can be chosen to stabilize the fatty acid-acylated insulin protein as a suspension in the propellant, to protect the active agent against chemical degradation, and the like. Suitable surfactants include sorbitan trioleate, soya lecithin, oleic acid, or the like. In some cases solution aerosols are preferred using solvents such as ethanol. Additional agents known in the art for formulation of a protein such as fatty acid-acylated insulin protein can also be included in the formulation.

The present invention also relates to a pharmaceutical composition including fatty acid-acylated insulin protein and suitable for administration by inhalation. According to the invention, fatty acid-acylated insulin protein can be used for manufacturing a composition or medicament suitable for administration by inhalation. The invention also relates to methods for manufacturing compositions including fatty acid-acylated insulin protein in a form that is suitable for administration by inhalation. For example, a dry powder formulation can be manufactured in several ways, using conventional techniques, such as described in any of the publications mentioned above and incorporated expressly herein by reference, and, for example, Baker, et al., U.S. Pat. No. 5,700,904, issued Dec. 23, 1997, the entire disclosure of which is incorporated expressly herein by reference. Particles in the size range appropriate for maximal deposition in the lower respiratory tract can be made by micronizing, milling, or the like. And a liquid formulation can be manufactured by dissolving the fatty acid-acylated insulin protein in a suitable solvent, such as water, at an appropriate pH, including buffers or other excipients.

The present invention may be better understood with reference to the following examples. These examples are intended to be representative of specific embodiments of the invention, and are not intended as limiting the scope of the invention.

EXAMPLE 1

Absorption of B29-Nε-Palmitoyl-Human Insulin Following Intravenous or Aerosol Administration in Dogs This study was conducted to compare administration of B29-Nε-palmitoyl-human insulin by inhalation with administration by intravenous injection. B29-Nε-palmitoyl-human insulin is a soluble human insulin derivative that has a prolonged hypoglycemic profile in normal pigs and pancreatized dogs comparable to Humulin® L (Lente®) insulin, which is a formulation containing insulin is an solid form that dissolves slowly after injection.

In this study, aerosols of B29-Nε-palmitoyl-human insulin were delivered to anesthetized dogs through an endotracheal tube via an ultrasonic nebulizer and a control group received a dose of B29-Nε-palmitoyl-human insulin by intravenous injection. Blood samples were collected at various time points after dosing to determine plasma concentrations of the test compound and bioavailability of inhaled material was determined. Dogs were chosen because they are large animals having respiratory tracts in which particles deposit in a manner similar to humans. Also, a large amount of data obtained in dogs following intravenous and subcutaneous administration of B29-Nε-palmitoyl-human insulin were available for comparative purposes.

Six male beagle dogs were used in this study. The animals were housed either two per cage or individually in stainless steel cages with suspended mesh floors. Initially, all dogs were fed approximately 450 g of Purina Certified Canine Diet 5007 each day. Animals were fasted approximately eight hours before dosing. After recovery from anesthesia, food and water were provided ad libitum until 48 hours post-dose. The initial daily feeding regimen was initiated at 48 hours post-dose. At study initiation, the animals weighed between 12.5 and 17.6 kg.

Each animal was dosed using two dosing regimens: a) intravenous injection (7 µg B29-Nε-palmitoyl-human insulin per kg of body weight) and b) aerosol delivery to the lung via an endotracheal tube (target lung does of 100 µg B29-Nε-palmitoyl-human insulin per kg of body weight). Following anesthesia using 2% Brevital®, each animal was intubated using a size 5 or 6 endotracheal tube. Aerosol delivery to the lung was achieved by connecting the endotracheal tube to an ultrasonic nebulizer (Model 25, Devilbiss Co., Somerset, Pa.) containing ~4 mg B29-Nε-palmitoyl-human insulin per mL of Humulin® R Diluent and 99mTc sulfur colloid. This system operated in a passive mode delivered the aerosol to the anesthetized animal through a one-way valve connected to the endotracheal tube. The target dose using the ultrasonic nebulizer was 100 µg/kg. Each animal was placed under a gamma camera for about a 37 minute exposure period in order to collect a scintiphoto of the lung to estimate total dose delivered.

Blood samples were collected at 0 (pre), 5, 10, 20, 40, 60, 120, 180, 240, 360, 480, 960, 1440, 2160, and 2880 minutes post-dose to measure B29-Nε-palmitoyl-human insulin in the blood. Blood samples were only collected until 1440 minutes post-dose after intravenous dosing. Serum concentration of immunoreactive B29-Nε-palmitoyl-human insulin was determined by a radioimmunoassay. Serum concentration of immunoreactive B29-Nε-palmitoyl-human insulin in dogs prior to the exposure of the drug is a measure of the endogenous insulin level, because the antiserum used in the radioimmunoassay recognized insulin as well as B29-Nε-palmitoyl-human insulin. Particle size distribution was determined using a Sierra cascade impactor (model 218-K ambient cascade impactor, Sierra Instruments, Carmel Valley, Calif.).

Estimated deposited lung doses ranged from 10.2 to 60.3 µg B29-Nε-palmitoyl-human insulin per kg of body weight as determined by gamma camera scintigraphy. The mass median aerodynamic diameter (MMAD) was estimated to be 5.67 µm, with a geometric standard deviation of 2.04 µm.

Pharmacokinetic parameters were calculated from validated software programs at Lilly Research Laboratories, Indianapolis, Ind. Serum concentrations below the quantitation limit (BQL) of 17 pM were assigned a zero value for the subsequent calculations except when the average of the pre-dose levels was calculated where BQLs were not used.

Area under the curve (AUC) values were determined in two ways. In the first method, the area under the curve was calculated only from 0 to 16 hours post-dose [AUC (0–16 h)]. The time was limited to 16 hours because most of the serum concentrations for t≦16 hr were much higher than two standard deviations above the average pre-dose levels, and because the serum concentration 24 hours post-dose were near baseline level (≦110 pM) for some dogs an receiving an intravenous dose. For other dogs, serum concentrations did rise at 24 hours post-dose, which may be related to the feeding schedule of these dogs.

In the second method, the area under the curve was calculated from 0 to t hours post-dose [AUC (0–t h). The time "t" was defined as the last time point at which the serum concentration appeared to be higher than the baseline insulin level (i.e., ~110 pM). The actual points not used in the AUC calculations are indicated by (**) in Table 1.

TABLE 1

Serum Concentrations of Immunoreactive B29-Nε-palmitoyl-human insulin in Male Beagle Dogs Following a Single Dose by Inhalation or Intravenous Administration Serum Immunoreactive B29-Nε-palmitoyl-human insulin Concentration (pM)

| (min) | Animal No. | | | | | | Mean | SE |
|---|---|---|---|---|---|---|---|---|
|  | 1 | 2 | 3 | 4 | 5 | 6 | | |
| Inhalation | | | | | | | | |
| 0 | 36.6 | 68.7 | 45.6 | 101 | 80.7 | 37.6 | 62 | 11 |
| 5 | 104 | 711 | 72.3 | 323 | 127 | 249 | 264 | 97 |
| 10 | 117 | 906 | 155 | 366 | 93 | 89.9 | 288 | 131 |
| 20 | 177 | 1093 | NR | 478 | 108 | 233 | 432 | 174 |
| 40 | 338 | 1891 | 525 | 709 | 223 | 351 | 673 | 253 |
| 60 | 549 | 2274 | 354 | 1109 | 312 | 199 | 600 | 323 |
| 120 | 921 | 2041 | 1307 | 1390 | 464 | 1225* | 1225 | 214 |
| 180 | 1155 | 1692 | 1742 | NR | 287 | 254 | 1026 | 325 |
| 240 | 1308 | 1335 | 2208 | 3365* | 968 | 318 | 1564 | 435 |
| 360 | 604* | 1216* | 1513* | 1618* | 835* | 300* | 1014 | 213 |
| 480 | 399* | 706* | 720* | 1300* | 498* | 339* | 660 | 143 |
| 960 | 204* | 333* | 218* | 453* | 154* | 201* | 261 | 46 |
| 1440 | 181 | 123 | 758 | 81.7 | NR | 25.1 | 234 | 134 |

TABLE 1-continued

Serum Concentrations of Immunoreactive B29-Nε-palmitoyl-human insulin in Male Beagle Dogs Following a Single Dose by Inhalation or Intravenous Administration Serum Immunoreactive B29-Nε-palmitoyl-human insulin Concentration (pM)

| (min) | 1 | 2 | 3 | 4 | 5 | 6 | Mean | SE |
|---|---|---|---|---|---|---|---|---|
| 2160 | 456 | 161 | 552 | 301 | 196 | 259 | 321 | 62 |
| 2880 | 26.1** | 64.4** | 90.9** | 49.5** | NR** | NR** | 58 | 14 |
| Intravenous | | | | | | | | |
| 0 | BQL | 22.7 | 72.9 | 71.5 | BQL | BQL | 28 | 14 |
| 5 | 16647 | 12426 | 23417 | 12853 | NR | 16978 | 16464 | 1975 |
| 10 | 14688 | 25895 | 17038 | 15900 | 13744 | 7665 | 15822 | 2416 |
| 20 | 10894 | 12133 | 16496 | 17400 | 11762 | 3969 | 12109 | 1959 |
| 40 | 11647 | 7146 | 5676 | 12350 | 8069 | 9736 | 9104 | 1066 |
| 60 | 8526 | 5887 | 9468 | 4162 | 14133 | 3430 | 7601 | 1625 |
| 120 | 2715* | 2951 | 3363 | 3067 | 3508 | 1757 | 2894 | 255 |
| 180 | 2084 | 1655* | 2000* | 2048* | 2147 | 1345 | 1880 | 128 |
| 240 | 1385* | 1172* | 1056* | 1244* | 1480* | 1261* | 1266 | 61 |
| 360 | 900* | 780* | 1018* | 1089* | 1029* | 901* | 953 | 46 |
| 480 | 824* | 604* | 675* | 751* | 646* | 735* | 706 | 33 |
| 960 | 2699 | 2090 | 5614 | 721 | 109* | 257* | 1915 | 852 |
| 1440 | 90.6** | 3349 | 1277 | 7145 | 45.4** | BQL** | 1985 | 1159 |

BQL: below quantitation limit (17 pM)
NR: No result because of insufficient amount of sample
*Data points used in half-life determination
**Data points not used in AUC determination (for the second method)

TABLE 2

Pharmacokinetic Parameters of B29-Nε-palmitoyl-human insulin in Male Beagle Dogs Following a Single Dose by Inhalation or Intravenous Administration

| | Animal No. | | | | | | | |
|---|---|---|---|---|---|---|---|---|
| | 1 | 2 | 3 | 4 | 5 | 6 | Mean | SE |
| Inhalation | | | | | | | | |
| Dose (μg/kg) | 25.3 | 32.7 | 57.0 | 60.3 | 10.2 | 32.7 | 36.4 | 19.1 |
| AUC 0–16 (*) (nM*hr) | 8.6 | 15.6 | 14.4 | 21.5 | 7.3 | 5.4 | 12.1 | 6.1 |
| AUC/dose 0–16 h (nM*hr/μg/kg) | 0.34 | 0.48 | 0.25 | 0.36 | 0.72 | 0.17 | 0.39 | 0.079 |
| Bioavailability 0–16 h (%) | 6.1 | 10.2 | 3.4 | 8.3 | 16.3 | 5.7 | 8.3 | 1.8 |
| AUC 0–t (**) (nM*hr) | 14.0 | 19.2 | 26.1 | 26.0 | 10.8 | 8.0 | 17.4 | 7.7 |
| AUC/dose 0–t (nM*hr/μg/kg) | 0.55 | 0.59 | 0.46 | 0.44 | 1.06 | 0.24 | 0.56 | 0.11 |
| Bioavailability 0–t (%) | 9.9 | 7.5 | 4.1 | 4.9 | 24.0 | 8.41 | 9.8 | 3.0 |
| Cmax (nM) | 1.31 | 2.27 | 2.21 | 3.37 | 0.97 | 1.23 | 1.89 | 0.90 |
| Cmax/dose (nM/μg/kg) | 0.052 | 0.070 | 0.039 | 0.056 | 0.095 | 0.038 | 0.058 | 0.009 |
| Tmax (hr) | 4 | 1 | 4 | 4 | 4 | 2 | 3.2 | 0.5 |
| T ½ (hr) | 6.8 | 5.8 | 3.8 | 4.5 | 4.3 | 6.2 | 5.0*** | 1.2 |
| Intravenous | | | | | | | | |
| Dose (μg/kg) | 7 | 7 | 7 | 7 | 7 | 7 | | |
| AUC 0–16 h (nM*hr) | 39.1 | 32.9 | 51.2 | 30.1 | 30.9 | 20.4 | 34.1 | 4.2 |
| AUC/dose 0–16 h (nM*hr/μg/kg) | 5.6 | 4.7 | 7.3 | 4.3 | 4.4 | 2.9 | 4.88 | 0.60 |
| AUC 0–t (nM*hr) | 39.1 | 54.7 | 78.8 | 61.6 | 30.9 | 20.4 | 47.6 | 8.8 |
| AUC/dose 0–t (nM*hr/μg/kg) | 5.6 | 7.8 | 11.3 | 8.8 | 4.4 | 2.9 | 6.80 | 1.25 |
| Cmax (nM) | 16.6 | 25.9 | 23.4 | 17.4 | 14.1 | 17.0 | 19.1 | 0.19 |
| Cmax/dose (nM/μg/kg) | 2.38 | 3.70 | 3.35 | 2.49 | 2.02 | 2.43 | 2.73 | 0.27 |
| Tmax (hr) | 0.1 | 0.2 | 0.1 | 0.3 | 1 | 0.1 | 0.3 | 0.1 |
| T ½ (hr) | 3.4 | 3.5 | 3.8 | 3.9 | 3.2 | 5.3 | 3.7*** | 0.6 |

*AUC 0–16 h = area under the curve from time = 0 to 16 hr.
**AUC 0–t = area under the curve from time = 0 to t, where t is the time point whose serum B29-Nε-palmitoyl-human insulin concentration appeared to be higher than the average baseline level of the endogenous insulin level.
***Harmonic mean
SE: standard error of the mean The apparent pre-dose serum levels of B29-Nε-palmitoyl-human insulin (60±25 pM) represent measurements of endogenous insulin. These levels are similar to pre-dose levels of insulin measured in previous studies. Cmax values were achieved at approximately 3.2 hours post-dose, ranged from 0.0375 to 0.0949 nM/μg/kg, and averaged 0.058±8.8 nM/μg/kg.

After reaching peak values, the concentration of immunoreactive material then declined steadily dropping to half the maximum concentration at approximately five hours after dosing. Generally, B29-Nε-palmitoyl-human insulin serum concentrations returned to baseline level by 24 or 48 hours post-dose for dogs receiving B29-Nε-palmitoyl-human insulin by intravenous administration or inhalation, respectively.

T½ (half-life) values for inhalation were comparable to those obtained by intravenous administration, and were on the order of several hours (Table 2). T½ values in the present study were comparable to those measured in a previous study following subcutaneous administration of B29-Nε-palmitoyl-human insulin.

As mentioned above, AUC (0–t) values were determined in two ways. Using the first method of AUC determination, the bioavailability of inhaled B29-Nε-palmitoyl-human insulin in individual dogs ranged from 3.4% to 16.3% (Table 2), with an average of about 8%. Using the second method of AUC etermination, the bioavailability of inhaled B29-Nε-palmitoyl-human insulin in individual dogs ranged from 4.1% to 24.0%, with an average of about 10%.

The bioavailability of B29-Nε-palmitoyl-human insulin administered by the pulmonary route can be compared with the bioavailability of the same molecule, given subcutaneously in a previous study. Following a single subcutaneous dose of 0.05 mg/kg B29-Nε-palmitoyl-human insulin to male and female dogs, the average AUC (0–24 hr) was determined to be 122.8 nM*hr, or ~2.46 nM*hr/μg/kg. Thus, the relative bioavailability of inhaled B29-Nε-palmitoyl-human insulin is about 23% that obtained by subcutaneous administration. To determine this relation, the average AUC(0–t) value for inhalation was normalized for the dose administered, because the average AUC value for the subcutaneous dose was calculated based on drug concentrations from 0–24 hours.

The absorption of the acylated insulin after pulmonary administration is estimated at 11–14% compared with subcutaneous administration. This estimate was determined by dividing the absolute bioavailability of 8–10% by the 74% relative bioavailability of subcutaneous to intravenous administration determined in pancreatized dogs. In a previous study (Pillai, et al., (1996) *J. Aerosol Medicine*, 9:227–240.), it was shown that inhalation of 4 μm MMAD insulin aerosols produced a bioavailability of 38% relative to subcutaneous administration, while 1 μm MMAD insulin aerosols had a bioavailability of 100% relative to subcutaneous.

The present study has demonstrated that there is substantial bioavailability of B29-Nε-palmitoyl-human insulin (11% to 23%, based on AUC) delivered to dogs by inhalation of 5.7 μm MMAD aerosols compared to subcutaneous injection. These findings indicate that aerosol delivery of B29-Nε-palmitoyl-human insulin results in good relative bioavailability when the particle size distribution is small enough for the particles to reach the alveolar region of the lung. Bioavailability and absorption would likely be improved with an aerosol delivery system that achieved particle-sizes of 1–2 μm MMAD, or 2–3 μm MMAD.

EXAMPLE 2

Comparison of Inhalation with Subcutaneous Administration

This study was conducted to demonstrate that two fatty acid-acylated insulins are long-acting when administered either by inhalation or subcutaneously. Inhalation studies with both B28-Nε-myristoyl-LysB28,ProB29-human insulin analog and B29-Nε-palmitoyl-human insulin were carried out in beagle dogs by methods similar to those described in Example 1. In each case, blood levels were measured following inhalation and compared to those obtained following subcutaneous administration. The subcutaneous doses were 15 μg/kg (0.4 U/kg) for B28-Nε-myristoyl-LysB28,ProB29-human insulin analog and 50 μg/kg (1.4 U/kg) for B29-Nε-palmitoyl-human insulin. The mean inhaled doses, determined by gamma camera scintigraphy of a Tc-99m radiolabel uniformly dispersed in the inhaled aerosols, were 222 μg/kg for B28-Nε-myristoyl-LysB28, ProB29-human insulin analog and 36 μg/kg for B29-Nε-palmitoyl-human insulin.

Table 3 shows serum immunoreactive levels of B28-Nε-myristoyl-LysB28,ProB29-human insulin analog and blood glucose levels following administration by pulmonary or subcutaneous delivery. These data show that the pharmacokinetic profile (e.g., Tmax and T½) and the pharmacodynamic profile (e.g., blood glucose control) are remarkably similar for the inhaled and subcutaneous modes of administration. This similarity could not have been predicted from previous work on administration of insulin and insulin analogs via the lung. Such similarity is useful to the physician and to the patient.

TABLE 3

Serum Concentrations of Immunoreactive B28-Nε-myristoyl-LysB28, ProB29-human insulin analog and Glucose Levels in Male Beagle Dogs Following a Single Dose by Inhalation (221 μg/kg) or Subcutaneous Administration (15 μg/kg)

| | Serum Immunoreactive Insulin Analog (pM) | | Blood Glucose Concentration (mg/dL) | |
|---|---|---|---|---|
| Time (min) | Mean | SE | Mean | SE |
| Inhalation (221 μg/kg) | | | | |
| 0 | 25.5 | 4.7 | 100 | 0 |
| 5 | 441 | 108 | 102 | 5 |
| 10 | 511 | 78 | 99 | 4 |
| 20 | | | 96 | 5 |
| 40 | 1544 | 400 | 75 | 3 |
| 60 | 1754 | 338 | 73 | 8 |
| 120 | 2982 | 576 | 52 | 5 |
| 180 | 3103 | 682 | 52 | 8 |
| 240 | 2906 | 723 | 50 | 11 |
| 360 | 2501 | 588 | 81 | 7 |
| 480 | 1796 | 245 | 80 | 13 |
| 960 | 839 | 117 | 97 | 6 |
| 1440 | 221 | 48 | 101 | 6 |
| Subcutaneous (15 μg/kg) | | | | |
| 0 | 35 | 13 | 100 | 0 |
| 5 | 61 | 46 | 105 | 3 |
| 10 | 112 | 67 | 109 | 5 |
| 20 | 192 | 57 | 108 | 4 |
| 40 | 585 | 271 | 105 | 7 |
| 60 | 951 | 278 | 109 | 9 |
| 120 | 1484 | 404 | 101 | 4 |

TABLE 3-continued

Serum Concentrations of Immunoreactive B28-Nε-myristoyl-LysB28, ProB29-human insulin analog and Glucose Levels in Male Beagle Dogs Following a Single Dose by Inhalation (221 μg/kg) or Subcutaneous Administration (15 μg/kg)

| Time (min) | Serum Immunoreactive Insulin Analog (pM) | | Blood Glucose Concentration (mg/dL) | |
|---|---|---|---|---|
|  | Mean | SE | Mean | SE |
| 180 | 1831 | 525 | 97 | 6 |
| 240 | 1490 | 401 | 91 | 3 |
| 360 | 1622 | 593 | 93 | 10 |
| 480 | 1200 | 665 | 105 | 8 |
| 960 | 472 | 153 | 100 | 7 |
| 1440 | 97 | 33 | 111 | 7 |

TABLE 4

Serum Concentrations of Immunoreactive B29-Nε-palmitoyl-human insulin in male beagle dogs following a single dose by inhalation (36 μg/kg) or Subcutaneous Administration (50 μg/kg)

| Time (h) | Serum Immunoreactive Insulin Analog (pM/μg/kg) | |
|---|---|---|
|  | Mean | SE |
| Inhalation (36 μg/kg) | | |
| 0 | 1.7 | 0.3 |
| 1 | 22.0 | 8.9 |
| 2 | 33.7 | 5.9 |
| 3 | 28.2 | 8.9 |
| 4 | 43.5 | 12.0 |
| 6 | 27.9 | 5.9 |
| 8 | 18.1 | 3.9 |
| 16 | 7.2 | 1.3 |
| 24 | 6.4 | 3.7 |
| Subcutaneous (50 μg/kg) | | |
| 0 | 1.1 | 0.3 |
| 1 | 179 | 17.6 |
| 3 | 247 | 27.0 |
| 6 | 218 | 29.3 |
| 8 | 176 | 26.4 |
| 10 | 102 | 16.4 |
| 12 | 80 | 14.5 |
| 16 | 31 | 5.3 |
| 24 | 10 | 2.2 |

The relative bioavailability of B28-Nε-myristoyl-LysB28, Pro29-human insulin analog deposited in the lung compared to that injected subcutaneously was 11.2% as determined by comparing the maximum blood levels when normalized for the same dose delivered to the body, i.e., either deposited in the lung below the trachea or injected subcutaneously into the body. The relative bioavailability of inhaled to subcutaneous B29-Nε-palmitoyl-human insulin was 22%. These relative bioavailabilities of 11% and 22% should be compared to the values of approximately 40% to 50% for non-acylated insulin that have been observed in previous animal studies conducted at Eli Lilly [Pillai, R. S., et al., *J. of Aerosol Med.*, 9:227–240 (1996)] and also in human clinical trials [Patton, J. S., et al., *Respiratory Drug Delivery IV*, Interpharm Press. Buffalo Grove, Ill. (1994), pp. 65–74]. These two publications are incorporated herein by reference.

Both B28-Nε-myristoyl-LysB28,ProB29-human insulin analog and B29-Nε-palmitoyl-human insulin are well-absorbed through the dog lung. Although the degree of absorption is less than that of non-acylated insulin, the fatty acid-acylated insulins are absorbed in an amount effective to reduce glucose levels. The pharmacokinetics of the subcutaneous and inhaled insulins are quite similar for fatty acid-acylated insulins. One of skill in the art recognizes from these data that other fatty acid-acylated insulins and fatty acid-acylated insulin analogs are also absorbed from the lung, since these data are obtained with two representative molecules. These data also create in the person of skill in the art the reasonable expectation that these types of molecules can be administered by inhalation, that particles having properties known to make them likely to deposit in the lungs of a patient would be deposited in the lung of a human patient in need of these molecules to control blood glucose, and that these molecules would be absorbed into the patient's blood from the deposited particles.

The invention has been described with reference to various specific and preferred embodiments and techniques. However, it should be understood that many variations and modifications may be made while remaining within the spirit and scope of the invention. All publications and patent applications in this specification are indicative of the level of ordinary skill in the art to which this invention pertains.

We claim:

1. A pharmaceutical formulation comprising a fatty acid-acylated human insulin or a fatty acid-acylated human insulin analog and a liquid carrier, for administration by inhalation to a patient in need thereof.

2. The formulation according to claim 1, wherein the fatty acid-acylated human insulin or fatty acid-acylated human insulin analog is acylated with a fatty acid having ten to sixteen carbon atoms.

3. The formulation according to claim 2, wherein the fatty acid-acylated human insulin or fatty acid-acylated human insulin analog is selected from the group consisting of B29-Nε-myristoyl-human insulin, B29-Nε-palmitoyl-human insulin, B28-Nε-myristoyl-LysB28,ProB29-human insulin analog, and B29-Nε-myristoyl-des(ThrB30)-human insulin analog.

4. The formulation according to claim 3, wherein the fatty acid-acylated human insulin analog is B29-Nε-myristoyl-des(ThrB30)-human insulin.

5. The formulation according to claim 1, further comprising a non-acylated insulin or insulin analog.

6. The formulation according to claim 5, wherein the non-acylated insulin is human insulin.

7. The formulation according to claim 5, wherein the non-acylated insulin analog is LysB28,ProB29-human insulin.

8. The formulation according to claim 5, wherein the non-acylated insulin analog is AspB28-human insulin.

9. The formulation according to claim 1, wherein the formulation is an aqueous solution or an aqueous suspension of the fatty acid-acylated human insulin or fatty acid-acylated human insulin analog.

10. The formulation according claim 1, further comprising zinc ions.

11. A method of delivering a fatty acid-acylated human insulin or fatty acid-acylated human insulin analog, comprising the step of using an inhalation device to deposit in the lungs of a patient in need thereof an effective amount of a pharmaceutical formulation comprising a fatty acid-acylated human insulin or a fatty acid-acylated human insulin analog and a liquid carrier.

12. The method according to claim 11, wherein the fatty acid-acylated human insulin or fatty acid-acylated human insulin analog is acylated with a fatty acid having ten to sixteen carbon atoms.

13. The method according to claim 12, wherein the fatty acid-acylated human insulin or fatty acid-acylated human insulin analog is selected from the group consisting of B29-Nε-myristoyl-human insulin, B29-Nε-palmitoyl-human insulin, B28-Nε-myristoyl-LysB28,ProB29-human insulin analog, and B29-Nε-myristoyl-des(ThrB30)-human insulin analog.

14. The method according to claim 13, wherein the fatty acid-acylated human insulin analog is B29-Nε-myristoyl-des(ThrB30)-human insulin.

15. The method according to claim 11, wherein the formulation further comprises a non-acylated insulin or insulin analog.

16. The method according to claim 15, wherein the non-acylated insulin is human insulin.

17. The method according to claim 15, wherein the non-acylated insulin analog is LysB28,ProB29-human insulin.

18. The method according to claim 15, wherein said non-acylated insulin analog is AspB28-human insulin.

19. The method according to claim 11, wherein the formulation is an aqueous solution or an aqueous suspension of the fatty acid-acylated human insulin or fatty acid-acylated human insulin analog.

20. The method according to claim 11, wherein the formulation further comprises zinc ions.

21. The method according to claim 11, wherein the inhalation device is a nebulizer or a sprayer.

22. A pharmaceutical formulation comprising a fatty acid-acylated human insulin or a fatty acid-acylated human insulin analog in dry powder form, for administration by inhalation to a patient in need thereof.

23. The formulation according to claim 22, wherein the dry powder comprises particles of the fatty acid-acylated human insulin or fatty acid-acylated human insulin analog having an MMEAD of less than 10 μm.

24. The formulation according to claim 23, wherein the MMEAD is in the range of about 1 μm to about 5 μm.

25. The formulation according to claim 24, wherein the MMEAD is in the range of about 1 μm to about 3 μm.

26. The formulation according to claim 25, wherein the MMEAD is in the range of about 2 μm to about 3 μm.

27. The formulation according to claim 22, wherein the fatty acid-acylated human insulin or fatty acid-acylated human insulin analog is acylated with a fatty acid having ten to sixteen carbon atoms.

28. The formulation according to claim 27, wherein the fatty acid-acylated human insulin or fatty acid-acylated human insulin analog is selected from the group consisting of B29-Nε-myristoyl-human insulin, B29-Nε-palmitoyl-human insulin, B28-Nε-myristoyl-LysB28,ProB29-human insulin analog, and B29-Nε-myristoyl-des(ThrB30)-human insulin analog.

29. The formulation according to claim 28, wherein the fatty acid-acylated human insulin analog is B29-Nε-myristoyl-des(ThrB30)-human insulin.

30. The formulation according to claim 22, further comprising a non-acylated insulin or insulin analog.

31. The formulation according to claim 30, wherein the non-acylated insulin is human insulin.

32. The formulation according to claim 30, wherein the non-acylated insulin analog is LysB28,ProB29-human insulin.

33. The formulation according to claim 30, wherein the non-acylated insulin analog is AspB28-human insulin.

34. The formulation according to claim 22, wherein the formulation further comprises zinc ions.

35. A method of delivering a fatty acid-acylated human insulin or fatty acid-acylated human insulin analog, comprising the step of using an inhalation device to deposit in the lungs of a patient in need thereof an effective amount of a pharmaceutical formulation comprising a fatty acid-acylated human insulin or a fatty acid-acylated human insulin analog in dry powder form.

36. The method according to claim 35, wherein the dry powder comprises particles of the fatty acid-acylated human insulin or fatty acid-acylated human insulin analog having an MMEAD of less than 10 μm.

37. The method according to claim 36, wherein the MMEAD is in the range of about 1 μm to about 5 μm.

38. The method according to claim 37, wherein the MMEAD is in the range of about 1 μm to about 3 μm.

39. The method according to claim 38, wherein the MMEAD is in the range of about 2 μm to about 3 μm.

40. The method according to claim 35, wherein the fatty acid-acylated human insulin or fatty acid-acylated human insulin analog is acylated with a fatty acid having ten to sixteen carbon atoms.

41. The method according to claim 40, wherein the fatty acid-acylated human insulin or fatty acid-acylated human insulin analog is selected from the group consisting of B29-Nε-myristoyl-human insulin, B29-Nε-palmitoyl-human insulin, B28-Nε-myristoyl-LysB28,ProB29-human insulin analog, and B29-Nε-myristoyl-des(ThrB30)-human insulin analog.

42. The method according to claim 41, wherein the fatty acid-acylated human insulin analog is B29-Nε-myristoyl-des(ThrB30)-human insulin.

43. The method according to claim 35, wherein the formulation further comprises a non-acylated insulin or insulin analog.

44. The method according to claim 43, wherein the non-acylated insulin is human insulin.

45. The method according to claim 43, wherein the non-acylated insulin analog is LysB28,ProB29-human insulin.

46. The method according to claim 43, wherein the non-acylated insulin analog is AspB28-human insulin.

47. The method according to claim 35, wherein the formulation further comprises zinc ions.

* * * * *